US006203671B1

(12) United States Patent
Demmin

(10) Patent No.: US 6,203,671 B1
(45) Date of Patent: Mar. 20, 2001

(54) METHOD OF PRODUCING FLUORINATED COMPOUNDS

(75) Inventor: Timothy R. Demmin, Erie County, NY (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/265,496

(22) Filed: Mar. 10, 1999

(51) Int. Cl.$^7$ .................................................. C07C 17/00
(52) U.S. Cl. .............................. 204/157.94; 204/158.11; 204/158.12
(58) Field of Search ........................... 204/157.6, 157.94, 204/157.98, 158.11, 158.12

(56) References Cited

U.S. PATENT DOCUMENTS

| | | | |
|---|---|---|---|
| 4,377,715 | 3/1983 | Nychka | 570/123 |
| 5,406,008 | 4/1995 | Sievert | 570/123 |

OTHER PUBLICATIONS

Tung, Hsueh Sung, Vapor–phase fluorination process and catalysts for the manufacture of 1,1,1,3,3–pentafluoropropane, 1998.

Tung, Hsuch Sung; Merkel Daniel Christopher; Dziadyk, Zenart Joseph; Carson, Clayton Herbert; Pham, Hang Thanh; Ellis, Lois Anne Shorts, Fluorination Process and Catalysts for the Manufacture of 1,1,1,3,3–pentafluoropropane and 1,1,1,3,3,3–hexafluoropropane from 1,1,1,3, 3–pentachloropropane and 1,1,1,3,3,3–hexachloropropane with recovery and process recycle of hydrogen fluoride, 1998.

Asaoka, Masanobu; Gofuku, Ihachiro; Ito, Yasuhiro; Nakazawa, Ikuo; Terada, Masahiro; Liquid crystal element and liquid crystal device, 1998.

Conte, L., Gambaretto, G. P.; Napoli, M.; Fraccaro, C.; Legnaro, E.; Liquid–phase fluorination of aromatic compounds by elemental fluorine, J. Fluorine Chem. (1995).

Syvret, Robert G.; Vassilaros, Daniel L.; Parees, David M.; Pez, Guido P.; The formation of halogenaed succinates by liquid–phase direct fluorination with elemental fluorine; J. Fluorine Chem. (1994).

Scherer, Kirby V., Jr.; Yamanouchi, Kouichi; Ono, Taizo; A new synthetic approach to perfluorochemicals; liquid phase photofluorination with elemental fluorine. Part I; J. Fluorine Chem. (1990).

Kasemann, R.; Naumann, D.;1 Low temperature liquid phase fluorination of pentafluorophenyl compounds. Preparation and properties of (C6F5)3AbF2, (C6F5)3Sbf2, (C6F5) 2SeF2, (C6F5)2SeO, C6F5TeF3 and Cs[(C6F5)3EF3] (E=arsenic, antimony), J. Fluorine Chem. (1998).

Ruppert, Ingo; Fluorinated heteroorganic compounds: direct oxidative liquid–phase fluorination. 5. Preparation of cis and trans isomeric diphenyl sulfur tetrafluoride by elemental fluorination of diphenyl sulfide; J. Fluorine Chem. (1979).

Ruppert, Ingo; Bastian, Volker; Fluorinated element–organics: oxidative liquid phase direct fluorination. 3. Difluoroarsoranes and homologous compounds R'R2EF2 (E=arsenic, antimony, bismuth) by oxidative direct fluorination of organoarsines, . stibines, and . bismuthines; Angew. Chem. (1978).

Hotchkiss, I. J.; Stephens, R.; Tatlow, J.C.; The actions of elemental fluorine of polyfluroolefins and aromatic compounds. Part III. The fluorination of pentafluoropyridine; J. Fluorine Chem. (1977).

Ono, Taizo; Yamanouchi, Kouichi; Fernandez, Richard E.; Scherer, Kirby V. Jr.; Liquid–phase photofluorination with elemental fluorine. Part III. Synthesis of perfluorocycloalkyl ethers with/without a chlorine substituent; J. Fluorine Chem. (1195).

Ono, Taizo; Yamanouchi, Kouichi; Scherer, Kirby V. Jr.; Synthesis of perfluorinated tertiary amines via liquid–phase photofluorination with elemental fluorine; J. Fluorine Chem. (1995).

Naumann, Dieter; Lange, Horst; Reaction of organomercury compounds with elemental fluorine: a new synthesis for organomercury fluorides RHgF; J. Fluorine Chem. (1983).

Makarov, S.P.; Ermakova, I. V.; Shpanskii, V.A.; Liquid–phase florination of acetonitrile by elemental fluorine; Zh. Obshch. Khim (1996).

Abstract–Scherer, Kirby V., Jr.; Yamanouchi, Kouichi; Ono, Taizo A New Synthetic Approach to Perfluorochemicals: Liquid Phase Photofluorination with Elemental Fluorine. Part I.(1990), Journal of Fluorine Chemistry (1190), 47–65, No Month Available.

Abstract –Lopez, M.I.; Castellano, E.; Schumacher, H.J. Kinetics of the Photochemical Fluorination of Carbonylfluoride. J. Photochem. (1974) 3(2–3), 97–106, No Month Available.

Tedder, "Direct Fluorination of Liquid Hydrocarbons and Their Derivatives", Chemistry & Industry, pp. 508–509.*

* cited by examiner

*Primary Examiner*—Edna Wong
(74) *Attorney, Agent, or Firm*—Colleen D. Szuch; Jay P. Friedenson

(57) ABSTRACT

A process for preparing a fluorinated product comprising: (a) reacting a molar excess of an aliphatic starting compound in liquid phase with fluorine in the presence of actinic radiation to produce a product mixture containing a fluorinated product having at least one hydrogen atom; and (b) recovering the fluorinated product from the product stream.

17 Claims, No Drawings

METHOD OF PRODUCING FLUORINATED COMPOUNDS

FIELD OF INVENTION

The invention relates generally to a process for preparing fluorinated compounds. More specifically, the present invention relates to fluorination using elemental fluorine to produce a hydrofluoroalkane or hydrochlorofluoroalkane, while minimizing formation of perhaloalkane by-products.

BACKGROUND OF THE INVENTION

The commercial potential for highly-fluorinated hydrofluorocarbons (HFCs), such as, 1,1,1,2,3,3,3-heptafluoropropane (HFC-227ea), continues to be realized. For example, HFC-227ea has been found to be useful semiconductor etchant gas. Accordingly, there is a need for commercially-viable processes of preparing these compounds.

Traditionally, these compounds have been produced using various fluorination processes depending upon the availability of the starting materials and the desired fluorinated product. One common approach, which is of particular interest herein, is fluorination using elemental fluorine. Elemental fluorination typically involves a thermally-catalyzed reaction of elemental fluorine with a hydrofluorocarbon (HFC) or a hydrochlorofluorocarbon (HCFC), in the vapor-phase. The production of such compounds using elemental fluorination, however, is hampered by the formation of perhalogenated by-products such as tetrafluoromethane and octafluoropropane.

In addition to consuming valuable starting materials, the formation of perhalogenated by-products presents environmental problems. More specifically, the atmospheric lifetime of perhalogenated compounds tends to be relatively long thereby contributing to global warming. Both in the United States and abroad, there is a concerted effort underway to limit the production of such compounds.

Therefore, there is a need to develop alternative processes for preparing hydrogen-containing, highly-fluorinated compounds while avoiding the generation of perhalogenated by-products. The present invention fulfills this need among others.

DETAILED DESCRIPTION OF THE PRESENT INVENTION

The present invention overcomes the problems of conventional elemental fluorination by using actinic radiation as a photoinitiator in a liquid-phase reaction where the substrate to be fluorinated also serves as the solvent. The reaction produces hydrofluoroalkanes or hydrochlorofluoroalkanes with little or no formation of perhalogenated by-products. Thus, the present invention provides a viable alternative to vapor-phase, thermal fluorination.

One aspect of the invention is the provision of a process for producing a fluorinated product such as a hydrofluoroalkane or hydrochlorofluoroalkane using liquid-phase fluorination catalyzed by actinic radiation. In a preferred embodiment, the process comprises: (a) reacting a molar excess of an aliphatic substrate or starting material in liquid phase with fluorine in the presence of actinic radiation to produce a product mixture containing a fluorinated product; and (b) recovering said product from said fluorinated product mixture.

Preferred aliphatic starting materials include those having the formula:

$$X-R-Y \tag{1}$$

wherein:
R is an unsubstituted or substituted $C_1$–$C_{10}$ divalent alkyl group having two or more hydrogen atoms; and
X and Y are independently selected from $R_h$, F, or Cl, wherein $R_h$, is a $C_1$–$C_{10}$ perhalogenated alkyl.

R may be substituted with, for example, halides, $C_1$–$C_5$ haloalkyls, haloalicyclics, haloaryls substituted haloaryls, nitros, tri-substituted aminos, amidos, cyanos, and haloalkoxys. Preferably, R is an unsubstituted $C_1$–$C_4$ divalent alkyl, for example, methylene (—$CH_2$—) and its homologs, such as, —$CH_2CH_2$—, and —$CH_2CH_2CH_2$—. More preferably, R is methylene.

Preferably, $R_h$ is a $C_1$–$C_5$ alkyl perhalogenated with chlorine, fluorine or a combination thereof More preferably, $R_h$, is a perfluorinated $C_1$–$C_3$ alkyl.

Particularly preferred compounds of Formula 1 include the following groups: Group One wherein R is methylene and X and Y are perfluorinated alkyls or X is a perfluorinated alkyl and Y is F, such as, for example, 1,1,1,3,3,3-hexafluoropropane (HFC-236fa), 1,1,1,2,2,4,4,4-octafluorobutane (HFC-338), and 1,1,1,2,2,3,3,4,4,5,-decafluoropentane (HFC-43(10)); and Group Two wherein R is methylene and X is a perhalogenated alkyl and Y is either Cl or F such that Formula 1 contains at least one chlorine, such as, for example, 1,1,1-trifluoro-2-chloroethane (HCFC-133a), 1,1,2-trifluoro-1-chloroethane (HCFC-133b) and 1,1,3-trichloro-1,3,3-trifluoropropane (HCFC-233). In a more preferred embodiment, the starting material belongs to Group One. The most preferred starting material is HFC-236fa. The starting materials described above are preferable because they tend to be commercially available and/or readily synthesized.

It is worthwhile noting that a fluorination reaction may be conducted with a starting material which is not covered by Formula 1, but which eventually becomes fluorinated to the extent that it is covered by Formula 1. In other words, as the reaction proceeds to the production of the fluorinated product, an intermediate along the way may be covered by Formula 1. For example, a compound having a terminal group such as methyl, which is not covered by Formula 1, may be fluorinated in the reaction such that its terminal group becomes fluorinated and thus covered by Formula 1. Therefore, it should be understood that the term "starting material" is not limited to the material initially fed to the reactor, but also covers intermediates that may be produced in the course of fluorination.

The fluorinated product is, of course, a more fluorinated version of the starting material. Thus, a starting material of Formula 1 will produce a fluorinated product having the formula:

$$X-R'-Y \tag{2}$$

wherein:
R' is R having at least one hydrogen replaced by fluorine and at least one hydrogen remaining; and
X and Y are the same as described above.

As with the starting material, particularly preferred compounds of Formula 2 include the following groups: Group One wherein R' is fluoromethylene and X and Y are perfluorinated alkyls or X is perfluorinated and Y is F, such as, for example, 1,1,1,2,3,3,3-heptafluoropropane (HFC-227ea), 1,1,1,2,2,3,4,4,4-nonafluorobutane (HFC-329), and 1,1,1,2,2,3,3,4,4,5,5,-undecafluoropentane (HFC-42(11)); and Group Two wherein R' is fluoromethylene and X is perhalogenated alkyl and Y is either Cl or F, such that Formula 2 contains at least one chlorine, such as, for example, 1,1,1,2-tetrafluoro-2-chloroethane (HCFC- 124a), 1,1,2,2,-tetrafluoro-1-chloroethane (HCFC-124) and 1,1,3-trichloro-1,2,3,3-tetrafluoropropane (HCFC-224). In a preferred embodiment, the hydrofluoroalkane product belongs to Group One. The most preferred product is HFC-227ea.

In preparing the fluorinated product, the reactants, which include the starting material in liquid phase and elemental fluorine, are contacted in a reactor in the presence of actinic radiation. For purposes of this invention, "actinic radiation" refers to light energy of the required wavelength, intensity and duration to catalyze, or initiate, fluorination. Preferably, the actinic radiation is ultra-violet (UV) radiation. The UV radiation has a wavelength preferably from about 200 to about 400 nm, more preferably from about 250 to about 350 nm, and still more preferably from about 275 to about 300 nm. The ultraviolet light preferably is introduced to the reaction mixture using techniques and apparatus known in the art, such as, for example, irradiating the reaction mixture through a suitably-UV-transparent window (for example, commercially-available quartz or crystalline calcium fluoride or barium fluoride), or circulating the gas-liquid mixture through a suitably-UV-transparent container in close proximity to a UV light source.

During photofluorination, a molar excess of starting material relative to fluorine should be present such that the starting material also acts as a reaction solvent for the elemental fluorine. Using the starting material as a reaction solvent has been found to improve the selectivity of the fluorinated product, thereby decreasing or totally suppressing perhaloalkane formation. Accordingly, a high molar ratio of starting material to fluorine is preferred from the standpoint of improving selectivity. On the other hand, however, high ratios tend to decrease the output or production per unit of occupied reaction volume. Therefore, the molar ratio should be chosen to strike a balance between selectivity and output. It has been found that a molar ratio of starting material to fluorine (cumulative) is preferably from about 2:1 to about 50:1, more preferably from about 5:1 to about 20:1, and even more preferably from about 8:1 to about 12:1.

It is worthwhile to note that although the process of the invention is used preferably to replace hydrogen with fluorine in a small portion of starting material to produce the desired fluorinated product with high selectivity, it can also be used to replace a molar equivalent of hydrogen in the starting material to create an intermediate. This intermediate thus becomes the solvent in the reaction, and, in effect, a new starting material. This new starting material, in turn, is photofluorinated to produce yet another intermediate or the desired fluorinated product. Therefore, it should be noted that the starting material, as mentioned above, is not necessarily the material initially fluorinated but may be an intermediate formed in the process. Accordingly, the amount of elemental fluorine introduced to the reaction depends upon whether the objective is first to fluorinate an organic compound to replace a molar equivalent of hydrogen to form an intermediate, in which case a molar equivalent of fluorine is warranted, or whether the objective is to fluorinate the starting material (or an intermediate) to produce the final product, in which case a sub-molar equivalent of elemental fluorine is preferred for improved selectivity.

To achieve a molar excess of starting material, the reactor may be initially charged with starting material and/or the starting material may be fed continuously to the reactor simultaneously with the introduction of the gas stream containing the elemental fluorine. If the reactor is not charged initially with an excess of starting material, the feed rate should be sufficient to replace the starting material consumed in the reaction or otherwise lost by exiting the reactor in the product stream such that a molar excess of starting material is maintained.

The elemental fluorine preferably is fed to the reactor along with an inert gas diluent, such as nitrogen or argon, in a gaseous, fluorine feed stream. The use of an inert gas diluent is a standard practice in the safe handling of elemental fluorine, which is one of the most reactive elements. It is preferable to disperse the gas feed stream into the liquid phase using methods that are known to those skilled in the art. For example, the gas may be released through a submersed finely-porous, metal fritted disk made of passivated metal materials such as nickel, stainless steel, or preferably Monel. The inert gas facilitates the fluorine's dispersion in the liquid phase and consequently improves selectivity and rate of reaction. It is preferable, however, to avoid an excess of inert gas which can reduce the concentration of $F_2$ in the fluorine feed stream to the extent that production of the desired hydrofluoroalkane or hydrochlorofluoroalkane suffers. Preferably, the concentration of $F_2$ in the fluorine feed stream is about 5 to about 80 volume percent and, more preferably from about 10 to about 50 volume percent.

Since liquid-phase fluorination tends to occur at or near the interface between the liquid starting material and the gaseous elemental fluorine, increasing the contact area of the reactants is preferable to increase the fluorination rate. To this end, it is preferable to agitate the reaction mixture such that fine bubbles of elemental fluorine gas are formed and entrained in the liquid starting material. Smaller bubbles provide increased surface area and entraining them in the reaction mixture provides for longer contact time, that is, they tend not to leave the reaction mixture as readily. Techniques and apparatus for agitating the liquid-phase reaction mixture are well known. For example, an impeller may be used to agitate a stream of gaseous elemental fluorine introduced to the reaction mixture through a submersed finely porous metal fritted disk.

The flow of the fluorine feed stream to the reactor should be such that the total amount of elemental fluorine that reacts with the starting material is less than a stoichiometric amount with respect to the organic staring material. Introducing excess fluorine may induce over-fluorination and cause perfluoroalkane formation.

For each mole of fluorine that reacts with starting material one mole of HF is produced. The HF may be easily removed from the liquid and vapor phases by methods known to those skilled in the art, including fractional distillation and scrubbing with aqueous base.

Particular reaction temperatures and pressures tend to vary based on the hydrofluoroalkane or hydrochlorofluoroalkane being fluorinated, and one skilled in the art can optimize such conditions without undue experimentation. Preferably, the reaction temperature is sufficiently low both to maintain the organic starting material as a liquid phase without undue pressure build up in the reactor, and to minimize over-fluorination and generation of undesired perhalocarbons. Preferably, the reaction pressure is not greater than about 5 psig to avoid the need for a pressure-rated reactor. For example, it has been found that in the fluorination of HFC-236fa to produce HFC-227ea, a reaction pressure of about one atmosphere is preferred.

Generally, cooler reaction temperatures are preferred to minimize the formation of perhalogenated by-products, and to maintain the starting material in the liquid state. For example, it has been found that in the fluorination of HFC-236fa to produce HFC-227ea, a reaction temperature of about −20 to about −5° C. is preferred, while a temperature of about−10 to about −5° C. is more preferred. At temperatures lower than −20° C. the fluorination is relatively slow and at temperatures above −1° C. the HFC-236fa vapor pressure is greater than one atmosphere and pressure-rated reactors usually are required.

Reaction (contact) times depend on several factors including the type of actinic radiation used, its intensity, reaction temperature, and reactor configuration with regard to gas-liquid contact parameters including bubble dimensions, gas-liquid contact time, and method for dispersion or agitation of the reaction components. For a continuous process or for a batch process, the reaction times typically range from about 1 second to about 60 seconds, and, preferably, from about 10 seconds to about 30 seconds.

The fluorinated product, for example, HFC-227ea, is isolated and purified by methods readily known to those skilled in the art. For example, on a laboratory scale, the exiting diluent gas contains unreacted fluorine and HFC-236fa as well as by-product HF and product HFC-227ea. The HF is scrubbed with aqueous caustic solution and fluorine is scrubbed with aqueous KI solution and the HFC mixture is condensed at −70° C. in a cold trap. Fractional distillation provides HFC-227ea and recovered HFC-236fa for recycle. In a commercial process, it also may be preferable to recover the fluorine and HF.

In accordance with the process of the present invention, good selectivity can be achieved. For example, in the production of HFC-227ea from HFC-236fa, the selectivity is preferably no less than about 75% and, more preferably, no less than about 90%. Additionally, in accordance with the present invention, there is little or no generation of perfluorinated by-products. The production of perfluorinated by-products is preferably no greater than about 5 wt % of the hydrofluoroalkane product and, more preferably, no greater than about 0.5 wt % of the hydrofluoroalkane product.

EXAMPLE 1

This example illustrates the fluorination process of the present invention. A 100 ml Teflon reactor having a standard Teflon-coated magnetic stirring bar and a 100-watt medium pressure mercury UV light was used to facilitate the reaction. The 100 ml Teflon reactor was initially charged with 30 ml of HFC-236fa at −20° C. The elemental fluorine ($F_2$), diluted to 5 volume % in nitrogen, was introduced into the reactor while stirring at a total flow rate of 40 cc/min through a submersed 50 micron Monel fritted gas dispersion disk. Reactor pressure was maintained at atmospheric and reactor temperature was maintained at −20 to −10° C. No reaction occurred in the absence of UV light. To initiate the reaction, the UV light from the 100-watt medium pressure mercury UV lamp, surrounded by a water-cooled quartz immersion well, was introduced to the reactor contents through a port containing a calcium fluoride window, or the lamp was merely placed directly beside the reactor. The gaseous product stream, exiting from the reactor, was scrubbed to remove HF and unreacted $F_2$ and then analyzed by in-line gas chromatography. Additionally, samples were collected in 50 cc cylinders for gas chromatography/mass spectrometry analysis. The analyses revealed a product stream composition of 2% (gc area %) HFC-227ea, 98% HFC-236fa, and 0.1% of an isomer of C6HF13. There were no detectable amounts of HFC-218 in the product stream.

Comparative Example 1

This example illustrates the generation of perfluoroalkanes typically associated with thermally-initiated, vapor-phase fluorination. The fluorination of HFC-236fa was conducted in the vapor phase at 75° C. using 10 volume % of fluorine in nitrogen at a total flow of 70 cc/min through a heated 24"×2" stainless steel 316 tubular reactor and a co-feed of HFC-236fa at a flow of 10 cc/min. Perfluoropropane was observed to accompany the formation of HFC-227ea such that the selectivities of HFC-227ea and perfluoropropane were 94% and 6%, respectively.

Comparative Example 2

This example illustrates the lack of significant fluorination in low-temperature vapor-phase fluorination. Fluorination of HFC-236fa was attempted in the vapor phase at 20° C. using 10 volume % of fluorine in nitrogen at a total flow of 22 cc/min through a 12' coil of ¼" PFA tubing wrapped around the 100 watt UV lamp, and a co-feed of HFC-236fa at a flow of 5 cc/min. In the absence of UV light, little or no reaction occurred.

Comparative Example 3

This example illustrates the formation of perfluorinated by-products in low-temperature vapor-phase fluorination in the presence of UV light. UV light was introduced to the process described above with respect to Comparative Example 2. However, the UV radiation initiated fluorination such that perfluoropropane was generated. The selectivities of HFC-227ea and perfluoropropane were 90% and 10%, respectively.

What is claimed is:

1. A process for preparing a fluorinated product comprising:
   (a) reacting a molar excess of an aliphatic starting material in liquid phase with elemental fluorine in the presence of ultraviolet radiation to produce a product stream containing a fluorinated product having at least one hydrogen atom, said starting material having the following formula:

X—R—Y

wherein:
   R is an unsubstituted or substituted $C_1$–$C_{10}$ divalent alkyl group having two or more hydrogens atoms; and
   X and Y are independently selected from $R_h$, F, or Cl, wherein $R_h$ is a perhalogenated alkyl; and
   (b) recovering said fluorinated product from said product stream, said fluorinated product having the following formula:

X—R'—Y;

wherein:
   R' is R with at least one hydrogen replaced by fluorine and at least one hydrogen remaining.

2. The process of claim 1, wherein R is methylene and X is a perfluorinated alkyl group.

3. The process of claim 2, wherein Y is a perfluorinated alkyl group or F.

4. The process of claim 3, wherein said starting material is 1,1,1,3,3,3-hexafluoropropane (HFC-236fa), 1,1,1,2,2,4,4-octafluorobutane (HFC-338), or 1,1,1,2,2,3,3,4,4,5-decafluoropentane (HFC-43(10)); and wherein said fluorinated product is 1,1,1,2,3,3,3-heptafluoropropane (HFC-227ea), 1,1,1,2,2,3,4,4,4-nonafluorobutane (HFC-329), or 1,1,1,2,2,3,3,4,4,5,5-undecafluoropentane (HFC-42(11)).

5. The process of claim 4, wherein the yield of said HFC-227ea is no less than about 70%.

6. The process of claim 5, wherein the selectivity of said HFC-227ea is no less than about 90%.

7. The process of claim 1, wherein X is a perhalogenated alkyl and Y is either Cl or F such that the starting material contains at least one chlorine.

8. The process of claim 7, wherein said starting material is 1,1,1-trifluoro-2-chloroethane (HCFC-133a), 1,1,2-trifluoro-1-chloroethane or 1,1,3-trichloro-1,3,3-trifluoropropane (HCFC-233); and wherein said fluorinated product is 1,1,1,2-tetrafluoro-2-chloroethane (HCFC-124a), 1,1,2,2,-tetrafluoro-1-chloroethane (HCFC-124) or 1,1,3-trichloro-1,2,3,3-tetrafluoropropane (HCFC-224).

9. The process of claim 1, wherein formation of perfluorinated by-products is no greater than about 5 wt % of said hydrofluoroalkane product.

10. The process of claim 9, wherein formation of perfluorinated by-products is no greater than about 0.5 wt % of said hydrofluoroalkane product.

11. The process of claim 1, wherein the reaction is conducted at about atmospheric pressure.

12. The process of claim 1, wherein the molar ratio of said starting material to said fluorine is no less than about 2:1.

13. The process of claim 12, wherein the molar ratio of said starting material to said fluorine is no less than about 5:1.

14. The process of claim 1, wherein the reactor is charged initially with said starting material.

15. The process of claim 14, wherein fluorine is added to the reaction along with an inert gas in a fluorine feed stream.

16. The process of claim 15, wherein the concentration of fluorine in said feed stream is about 5 to about 80 vol %.

17. The process of claim 1, wherein the contact time of said starting material and said fluorine is about 1 to about 60 seconds.

* * * * *